(12) United States Patent
Lizio et al.

(10) Patent No.: US 8,273,375 B2
(45) Date of Patent: Sep. 25, 2012

(54) MULTIPARTICLE PHARMACEUTICAL DOSAGE FORM FOR A LOW-SOLUBLE ACTIVE SUBSTANCES AND METHOD FOR PRODUCING SAID PHARMACEUTICAL DOSAGE FORM

(75) Inventors: Rosario Lizio, Rossdof (DE); Hans-Ulrich Petereit, Darmstadt (DE); Peter Langguth, Biebergemünd (DE); Marcus Knöll, Heidesheim (DE)

(73) Assignee: Evonik Roehm GmbH, Darmstadt (DE)

( * ) Notice: Subject to any disclaimer, the term of this patent is extended or adjusted under 35 U.S.C. 154(b) by 1179 days.

(21) Appl. No.: 11/572,720

(22) PCT Filed: Jul. 8, 2005

(86) PCT No.: PCT/EP2005/007427
§ 371 (c)(1),
(2), (4) Date: Feb. 6, 2008

(87) PCT Pub. No.: WO2006/010453
PCT Pub. Date: Feb. 2, 2006

(65) Prior Publication Data
US 2008/0166416 A1 Jul. 10, 2008

(30) Foreign Application Priority Data
Jul. 27, 2004 (DE) .......................... 10 2004 036 437

(51) Int. Cl.
*A61K 9/14* (2006.01)
*A61K 31/513* (2006.01)
*A61K 31/4439* (2006.01)
*A61K 31/55* (2006.01)

(52) U.S. Cl. ........ 424/494; 514/217; 514/342; 514/274; 424/498

(58) Field of Classification Search .................. None
See application file for complete search history.

(56) References Cited

U.S. PATENT DOCUMENTS

| | | | |
|---|---|---|---|
| 5,938,990 A | 8/1999 | Boyle et al. | |
| 2004/0224019 A1 | 11/2004 | Shefer et al. | |
| 2005/0163837 A1* | 7/2005 | Boehm et al. | 424/464 |
| 2006/0269605 A1 | 11/2006 | Lizio et al. | |
| 2007/0026082 A1* | 2/2007 | Lizio et al. | 424/490 |
| 2007/0042045 A1 | 2/2007 | Lizio et al. | |
| 2008/0026051 A1 | 1/2008 | Lizio et al. | |

FOREIGN PATENT DOCUMENTS

| | | |
|---|---|---|
| DE | 103 32 160 | 2/2005 |
| EP | 0 514 008 | 11/1992 |
| WO | 03/007913 | 1/2003 |
| WO | WO 2004/052339 A1 | 6/2004 |

OTHER PUBLICATIONS

U.S. Appl. No. 11/815,632, filed Aug. 6, 2007, Lizio, et al.
U.S. Appl. No. 11/721,399, filed Jun. 11, 2007, Lizio, et al.
Japanese Office Action issued Jan. 26, 2011, in Patent Application No. 2007-522954 (German translation only).
Office Action issued Feb. 10, 2012 in Canadian Patent Application No. 2,570,608.
International Preliminary Report on Patentability and Written Opinion issued Jan. 30, 2007 in PCT/EP2005/007427.

\* cited by examiner

*Primary Examiner* — Anne Gussow
*Assistant Examiner* — Thurman Wheeler
(74) *Attorney, Agent, or Firm* — Oblon, Spivak, McClelland, Maier & Neustadt, L.L.P.

(57) ABSTRACT

The invention relates to an oral multiparticle pharmaceutical dosage form in the form of a receptacle reducing the pH values of stomach, containing a plurality of pellets, particles, granules or agglomerates whose mean diameter ranges from 50 to 2500 μm substentially consisting of a) an internal matrix layer containing an active agent which is neither peptide or protein, nor the derivatives or conjugates thereof, a lipophilic matrix whose melting point is greater than 37° C. and a polymer with mucoadhesive effect, b) an external film coating substantially consisting of a polymer or an anionic copolymer which is optionally formulated with conventional pharmaceutical additives, wherein the active agent has a water solubility according to DAB 10, of at least 30 volume parts of water for one part by weight of the active agent and is coated with the lipophilic matrix and said active agent-containing lipophilic matrix is coated with a matrix made of a polymer with mucoadhesive effect. A method for producing the inventive multiparticle pharmaceutical dosage is also disclosed.

21 Claims, No Drawings

MULTIPARTICLE PHARMACEUTICAL DOSAGE FORM FOR A LOW-SOLUBLE ACTIVE SUBSTANCES AND METHOD FOR PRODUCING SAID PHARMACEUTICAL DOSAGE FORM

The invention relates to a multiparticle pharmaceutical form for low-solubility active substances other than peptides or proteins and their derivatives or conjugates, and to a process for the preparation of the pharmaceutical form.

PRIOR ART

WO 02/03955 describes pharmaceutical forms for sublingual active-substance application in the form of bioadhesive microspheres. The microspheres have a mean diameter of less than 50 µm and contain a non-crystalline active substance in a micromatrix embedded in a bioadhesive polymer. The bioadhesive polymer can be e.g. a cellulose, a chitosan or an acrylic copolymer.

WO 02/051390 describes some formulations with a lipophilic matrix and a large amount (over 70%) of monoglycerides, which permit a more efficient release of the active substance.

WO 02/64148 describes some formulations with a mucopolysaccharide, together with a process for their preparation. The mucopolysaccharide, e.g. heparin, is first combined with an adsorption intensifier such as a chitosan, and then given a coating that only dissolves in the intestinal fluid, so that the active substance can be released in the middle or lower sections of the small intestine. The material used for the coating that dissolves in the intestinal fluid can be e.g. an anionic acrylic copolymer of the type of Eudragit® L, S or L100-55. The formulations can comprise capsules tablets and granules.

WO 02/43767 describes oral pharmaceutical formulations for active substances in the form of physiologically active peptides. These formulations contain the active substance coupled to a carrier that takes it across the cell membrane, a pH-lowering agent, and/or a protease inhibitor, and also an acid-stable transport vehicle. The latter protects the pharmaceutical formulation as it passes through the patient's stomach, preventing contact with the proteases present in the stomach. The transport vehicle can be a capsule that is coated with acid-resistant Eudragit®L30 D-55.

WO 03/007913 describes oral multiparticle pharmaceutical forms which contain the active substance in the form of numerous "patches". The latter are made of a biocompatible material, are disk-shaped and have a diameter of 500 µm to 5 mm and a thickness of 100-1000 µm. They have two layers or sides, one that is only slightly permeable to water or body fluids and is made e.g. of ethyl cellulose, and another side, which contains the active substance, e.g. a peptide or protein and is possibly mixed with mucoadhesive polymers, such as for example chitosan, CMC, polyacrylic acid or pectin. The patches can be compressed to form a tablet or they can be filled into a capsule, which is additionally given a coating that is soluble in the intestinal fluid. The active-substance preparations can also be combined with "enhancers", such as fatty acids, fatty alcohols, esters, surface-active substances and protease inhibitors. The capsule dissolves at the site of action, e.g. in a specific intestinal section, releasing the patches there. The latter can adhere to the intestinal mucosa, using their mucoadhesive side, and can liberate the active substance to the intestinal mucosa in a delayed and targeted manner. The other side of the patches, which is only slightly permeable, is intended to give the active substance a certain protection against chemical or enzymatic inactivation from the side of the intestinal lumen, as well as to prevent the active substance from escaping to this side.

Problem and Solution

WO 03/007913 proposes a significant and noteworthy solution to the task of preparing oral pharmaceutical forms, especially in the case of active substances that are to be released in the intestinal lumen in order to exert their effect there. However, this solution has the disadvantage, among others, that it involves the complicated formation and production of two-layer patch structures. Even more unfavourable, though, is the preparation of the pharmaceutical form as capsules with a coating that resists the gastric juices but is soluble in the intestinal fluid. The fact is that if these capsules measure much more than 2.5 mm, their therapeutic effect is not sufficiently reproducible. The time the capsules take to pass through the stomach can vary greatly, and in any case the onset of action is delayed. Besides, the capsules themselves can dissolve—quickly or slowly—even when only part of their coating has dissolved. The disadvantages of both components—coating and capsule—are additive here, so that all in all the release of the patches is without control. In the state where the capsules are at least partly accessible to the intestinal fluid, they can either remain intact or suffer considerable mechanical disintegration, according to the prevailing intestinal contents or intestinal peristalsis. There may be either a sudden release of a large amount of the patches on the one hand, or an undesirably retarded liberation of the patches on the other hand, according to the disintegration or mechanical effects acting on the originally coated capsules. There is a need therefore for a much more controllable release of the active substance.

There is a special problem in the case of low-solubility active substances in the sense defined in German Pharmacopeia DAB 10. For purposes of the present invention, these are taken to be active substances whose water-solubility according to DAB 10 is such that at least 30 parts by volume of water are needed to dissolve 1 part by weight of active substance. Active substances that are peptides or proteins, or peptide and protein derivatives or conjugates are explicitly ruled out in the present invention for these form the subject of a different invention. Low-solubility active substances and those which are even less soluble in water present certain problems in the formulation of the pharmaceutical form but they mainly suffer from having a low bioavailability. Many active substances of this type can therefore be developed further only as parenteral formulations, e.g. as implants or injections. These have the appreciable disadvantage of a low patient compliance, or they are not developed further to the stage of marketable products at all, despite their demonstrable pharmacologic activity. When an oral dosage form of such an active substance is prepared with the well-known excipients, it can happen that a large part of the active substance is not absorbed by the body from the resulting formulation. The residual bioavailability depends to a great extent on the circumstances in each individual case, e.g. on the surrounding conditions and presumably also on the receiving organism itself and so may be subject to large variations. A therapeutically reliable administration is therefore impossible in many cases. There is hence a need for pharmaceutical forms with which low-solubility active substances can be better administered.

One of the aims of the present invention is therefore to provide a pharmaceutical form that is suitable for the targeted and effective release of low-solubility active substances, other than peptides and proteins and their derivatives and conjugates. This pharmaceutical form should permit reliable dosing and a good distribution in the intestinal lumen after a rapid passage through the stomach. The active substance in question should be well protected from physical, chemical and enzymatic inactivation and it should be released at the specific site of action in such a way that a large part of it can be absorbed by the body. The site of release ought to be variable with the therapeutic aim, and it should be possible to select it reliably.

The aim of the invention is achieved by means of an oral multiparticle pharmaceutical form in the form of a casing that disintegrates in the gastric pH range and contains numerous pellets, particles, granulates or agglomerates with a mean diameter of 50-2500 μm, which are essentially composed of:
- a) an inner matrix layer comprising an active substance other than a peptide or a protein and their derivatives or conjugates; a lipophilic matrix with a melting point of over 37° C.; and a mucoadhesive polymer,
- b) a film-applied outer coating, essentially consisting of an anionic polymer or copolymer, which can be optionally formulated with pharmaceutically customary excipients, characterized in that
the active substance has a water-solubility as defined in the German Pharmacopeia DAB 10 of at least 30 parts by volume of water for dissolve 1 part by weight of the active substance and is embedded in the lipophilic matrix, and the lipophilic matrix with its active substance is in turn embedded in a matrix made from the mucoadhesive polymer Realization of the Invention The invention relates to an oral multiparticle pharmaceutical form in the form of a casing, especially tablets, minitablets, capsules filled with pellets, or sachets or reconstitutable powders, which disintegrates in the gastric pH range and contains numerous pellets, particles, granules (also e.g. extrudates, coprecipitates) or agglomerates with a mean diameter of 50-2500 μm, preferably 100-1000 μm and especially 200-800 μm, which are essentially composed of:

An inner matrix layer a) comprises an active substance other than a peptide or a protein and their derivatives or conjugates, a lipophilic matrix with a melting point of over 37° C., and a mucoadhesive polymer. Optionally or generally the inner matrix layer in the lipophilic matrix or to formulate the mucoadhesive polymer can contain further pharmaceutically customary excipients. Such formulating auxiliaries are well known to the specialist in the field.

a film-applied outer coating b) essentially consists of an anionic polymer or copolymer, which can again optionally formulated with pharmaceutically customary excipients, for example separating agents and/or plasticizers. More than one anionic polymer or copolymer can also be present in the formulation.

The water-solubility of the active substance as defined in the German Pharmacopeia DAB 10 is at least 30 parts by volume of water for 1 part by weight of the active substance and is embedded in the lipophilic matrix. The lipophilic matrix with its active substance in turn is embedded in a matrix made from the mucoadhesive polymer.

The multiparticle pharmaceutical form is so formulated that its constituent pellets, particles, granules, including extrudates, coprecipitates or agglomerates, are released in the pH range prevailing in the stomach. The casing containing the pellets, particles, granules, including extrudates, coprecipitates or agglomerates and disintegrating in the gastric pH range can be e.g. capsules, gelatin capsules, tablets, e.g. compressed tablets, reconstitutable powders or sachets.

The properties of the outer coating are adjusted by the appropriate choice of the anionic polymer or copolymer and/or of its formulation with excipients and of its layer thickness in such a way that it—the outer coating—dissolves in the gut at a pH of 4.0-8.0, preferably pH 5.5-7.8 and especially 5.8-7.5 within 10-60 minutes and preferably within 20-40 minutes so that the mucoadhesive matrix layer is exposed can bind to the intestinal mucosa and can establish contact there between the enterocytes and the lipophilic matrix with its active substance. As a result of this the active substance can be absorbed by the body with or without components of the lipophilic matrix. The latter is so chosen that the active substance and the substance or substances forming the matrix do not differ from each other in their water-solubility as defined in the German Pharmacopeia DAB 10 by more than ±50%, in their distribution coefficient defined in Annexe V to EU Directive No. 67/548/EEC Point A.8 by more than ±60%, and/or in their HLB value, as measured by Marszall's method by more than ±80%.

The mucoadhesive polymer or copolymer is so chosen that, when the pH of the medium is within ±0.5 pH units and preferably ±0.8 pH units from the pH value at which the outer coating begins to dissolve, it—the mucoadhesive polymer or copolymer—possesses a mucoadhesive action $\eta_b$ of at least 150-1000 mPa·s and preferably 200-900 mPa·s and a water absorption of 10-750%, preferably 10-250% and especially 10-100% in 15 minutes, and the amount of active substance in the matrix layer constitutes at most 40 wt-% and especially 0.01-15 wt-% or 0.05-5 wt-% of the amount of mucoadhesive polymer.

The Inner Matrix Layer

The inner matrix layer acts as a carrier for the active substance. It also has the role to dissolve—or at least bind—the active substance in the lipophilic matrix, increasing its bioavailability as far as possible. Components of the inner layer can bind to the intestinal mucosa, using the mucoadhesive polymer matrix surrounding the lipophilic matrix, and the active substance can be absorbed into the body from there. Another function of the inner matrix layer is to protect the active substance from physical, chemical or enzymatic inactivation.

The inner matrix layer consists of two matrix components, namely:
- a) a lipophilic matrix component, in which the active substance is dissolved, dispersed, emulsified or simply mixed, and
- b) a mucoadhesive matrix component, in which the lipophilic matrix is embedded.

The inner lipophilic matrix component acts as a carrier for the active substance. It also has the role to dissolve—or at least to bind—the active substance in the lipophilic matrix, increasing its bioavailability as far as possible. Another function of the inner matrix layer is to protect the active substance from physical, chemical or enzymatic degradation and to promote drug penetration and absorption through the intestinal epithelium (enterocytes), so that the active substance can enter the body from there. This function relies on the lipids and/or amphiphilic substances present in the inner matrix layer.

The next matrix layer or core, made of mucoadhesive polymers in which the lipophilic matrix is embedded, acts as a second drug carrier. Another function of this layer or core is to bind the lipophilic matrix to the intestinal mucosa with the aid of its constituent mucoadhesive polymer, so that it can reach, via the mucus layer, the surfaces of the enterocytes from there hereby permitting a direct contact between the lipophilic matrix and the enterocytes. Another function of the mucoadhesive matrix or core is to further protect the lipophilic matrix from physical, chemical or enzymatic cleavage inactivation.

Active Substances/Formulation
Active Substances

The active substances used in the invention are especially those intended to act in or on the human or animal body for the following purposes:
1. to cure, alleviate, prevent or diagnose diseases, symptoms, damage to the body, or complaints caused by a disease
2. to establish the nature, state or functions of the body or psychological states
3. to replace active substances or body fluids produced by the human or animal body
4. to protect from, eliminate or render harmless pathogens, parasites or nonphysiological substances or
5. to influence the nature, state or functions of the body or psychological states.

The active substances used, which are no peptides or proteins or their derivatives or conjugates, can be free acids or bases. Their counter-ions can be for example physiological bases or acids, compatible alkaline earth metals or alkali metals, amines, and also for example acetate, adipate, ascorbate, alginate, benzoate, benzene sulfonate, bromide, carbonate, carboxy methyl cellulose (free acid), citrate, chloride, dibutyl phosphate, dihydrogen citrate, dioctyl phosphate, dihexadecyl phosphate, fumarate, gluconate, glucuronate, glutamate, bicarbonate, hydrogen tartrate, hydrochloride, hydrogen citrate, iodide, lactate, α-lipoate, malate, maleate, malonate, pamoate, palmitate, phosphate, salicylate, stearate, succinate, sulfate, tartrate, tannate, oleate or octyl phosphate.

The amount of active substance in the lipophilic matrix can be e.g. at most 90 wt-% and especially 1-60 wt-% or 5-50 wt-%. The lipophilic matrix with its active substance can constitute preferably 5-60 wt-% and especially 10-50 wt-% of the inner matrix layer a). Depending on the physicochemical properties of the active substance, such as for example its water/oil partition coefficient or its isoelectric point, the inner layer a) can additionally contain an efflux pump inhibitor such as for example ketoconazole or polyethylene 66012-hydroxystearate (Solutol®HS15).

The inner layer a) can also contain a penetration promoting substance, especially a plasticizer, such as for example triethyl citrate, acetyl triethyl citrate, diethyl sebacate, dibutyl sebacate, polymers such as Carbomer, chitosan, chitosan cysteine, sodium carboxymethylcellulose, N-trimethylated chitosan, Polycarbophil cysteine long-chain fatty acids, their esters (e.g. their mono- and diglycerides) and salts, such as lauric acid, lauryl sulfonic acid, palmitic acid, caprylic acid, capric acids, oleic acid, acyl carnitines, chelating agents like EDTA, salicylates, cyclodextrins polyacrylic acids, bile acids like cholic acid, cholyl taurine, cholyl sarcosine, chenodeoxycholic acid and their salts, such as sodium cholate, sodium glycocholate, sodium taurocholate, sodium taurodihydrofusidate, sodium glycoldihydro-fusidate, surface-active agents and emulsifiers such as Polysorbate 80 (Tween 80), polyethoxylated castor oil (Cremophor EL), polyethoxylated/polypropoxylated glycol (Pluronic® F68), *Zonula occludens* toxin (ZOT), and vitamins like vitamin E (tocopherol) or vitamin B12.

The inner layer a) can also contain enzyme inhibitors, such as for example lipase inhibitors, esterase inhibitors and/or glycolase inhibitors.

Mucoadhesive Polymers

The inner matrix layer a, also contains mucoadhesive polymers in which the lipophilic matrix with its active substance is incorporated or embedded. Suitable mucoadhesive polymers include especially a chitosan (chitosan itself and its derivatives, i.e. chitosans), (meth)acrylate copolymers with 20-45 wt-% of methyl methacrylate and 55-30 wt-% of methacrylic acid, celluloses, especially methyl celluloses, such as for example sodium carboxymethyl cellulose (e.g. Blanose® or Methocel®).

The mucoadhesive polymer is so chosen that, when the pH differs by ±0.5 pH units and preferably by ±0.3 pH units from the pH value at which the outer coating begins to dissolve, it—the mucoadhesive polymer—can absorb 10-750%, preferably 10-250% and especially 10-160% of water in 15 minutes Determination of the Mucoadhesive Characteristics Hassan and Gallo have described a suitable method for determining the mucoadhesive characteristics (see E. E. Hassan and J. M. Gallo: A simple Theological method for the in vitro assessment of mucin-polymer bioadhesive bond strength, *Pharma Res.*, 7, No. 5 (1990), p. 491). This method is based on the assumption that the viscosity (η, dynamic viscosity or viscosity coefficient) of a mixture formed between a polymer and mucin is different from the sum of viscosities of the individual components, i.e.

$$\eta_{polymer/mucin\ mixture} = \eta_{mucin} + \eta_{polymer} + \eta_b,$$

where $\eta_b$ is the viscosity difference. The greater this difference $\eta_b$, the stronger the mucoadhesive character. The viscosity of the individual components is first determined with the aid of a rotary viscometer, using a 0.5% (wt/wt) aqueous solution of the mucoadhesive polymer and a 15% solution of mucin derived from hog stomachs. To determine the mucoadhesive character $\eta_b$, the viscosity of mucin, the viscosity of the polymer, and the viscosity of their mixture are measured at the concentrations mentioned above.

The mucoadhesive polymer is so chosen that, when the pH differs by ±0.5H units and preferably by ±0.3 pH units from the pH value at which the outer coating begins to dissolve, its mucoadhesive effect, determined as the viscosity $\eta_b$, is 150-1000 mPa·s and preferably 150-600 mPa·s.

Hydration and Water Uptake

The degree of hydration of a polymer depends on the ability of the latter to absorb water. Polymers swell when they take up water. This is due to a disequilibrium between the chemical potential of water in the polymer and that of water in the surrounding medium. Owing to the osmotic pressure of the polymer, water is absorbed by it until an equilibrium is established between the inner and the outer phase. At that point the polymer is hydrated to an extent of 100%. In the case of polymers with a low average molecular weight, a solution is formed, whereas a gel is formed in the case of polymers with a high molecular weight, or in the case of a cross-linked polymer. The polymer can absorb up to ten times its own weight (1000%) of water before an equilibrium is reached.

Determination of the Percentage Water Uptake

The specialist in the field will be familiar with the determination of the percentage water uptake. A suitable method is described e.g. in Section 7.7.6, entitled "Aufsaugvermögen" [=Absorption capacity] in R. Voigt's "Lehrbuch der pharmazeutischen Technologie" [=Textbook of Pharmaceutical Technology], 5th revised ed., Verlag Chemie, Basle, 1984, p. 151. The method uses the Enslin apparatus, in which a glass filter funnel is connected to a graduated pipette with the aid of rubber tubing, the pipette being fully horizontal and level with the glass frit. In this case, the water uptake is taken to be 100% when 1 g of the mucoadhesive polymer absorbs 1 ml of water in 15 minutes.

Owing to the comparatively rapid water uptake or hydration and to the high degree of hydration, the rapid protection of the active substance and its immediate binding to the intestinal mucosa are ensured from the moment the outer coating begins to dissolve. The active substance should not be strongly bound to the mucoadhesive matrix, so that it can be immediately transferred from the intestinal mucosa into the body.

Controlling the pH of the Matrix that Contains the Mucoadhesive Polymer

With many mucoadhesive polymers, the mucoadhesivity depends on the pH. The pH of the matrix can be controlled by the addition of an acid, base or buffer system. Thus, the inner matrix can contain a chitosan as a mucoadhesive polymer which is added jointly with an acetate buffer system. An acetate/sodium acetate buffer, adjusted to e.g. pH 5.0-5.5/can be incorporated in the matrix as an additive, or else it can be applied to a core over which the matrix is placed. In this ways chitosan and its derivatives can also be used in combination with film-applied layers that begin to dissolve at higher pH values, such as for example 6.0-8.0. The low pH of the microenvironment of the matrix is retained despite the high pH of the surroundings. In this way, the mucoadhesivity of the polymer can be utilized in a pH range where the mucoadhesivity would otherwise be less intense or nonexistent. The advantage of this is that it ensures a certain degree of protection from enzymes whose pH optimum lies in a higher pH range. The same principle can also be used in the opposite way by raising the pH of the matrix by adding a base and combining it with a film-applied layer that dissolves at lower pH values.

Examples of Suitable Mucoadhesive Polymers

Suitable mucoadhesive polymers are chosen according to their mucoadhesivity and water absorption capacity. The mucoadhesivity of the polymers in the pH range in question should be at least $\eta_b$=150-1000 mPa·s, and their water absorption should be 10-750% in 15 minutes. A number of examples are listed in the following table.

Chitosan is suitable for example for use in an environment with a pH of 5.5 the duodenum) or in one with a different pH (the ileum or the colon), provided that the pH of the matrix has been adjusted to about 5.5 with the aid of e.g. a buffer system.

The (meth)acrylate copolymer listed in the table is better suited to a pH range of 7.2 than to a pH range of about 5.5.

Sodium alginate is suitable for a pH of about 5.5 but not for pH 7.2.

Sodium carboxymethylcellulose and cross-linked polyacrylic acid are suitable over a wide pH range extending from 5.5 to 7.2.

The outer coating b) formed of anionic (meth)acrylate copolymers

The film-applied outer layer b) formed of anionic polymers or copolymers resists the gastric juices and serves to protect the inner layer a) from them. The outer coating also protects the active substance from a possible physical, chemical or even enzymatic inactivation until the coating reaches an intestinal section (duodenum, jejunum, ileum or colon) where it begins to dissolve. The outer coating serves here in particular for gastrointestinal targeting, i.e. the specific release of the inner matrix layer to the required intestinal sections as a result of the pH value prevailing there. To prevent any interference with the release of the inner layer a), interactions between the (meth)acrylate copolymer in the outer layer and the active substance or the mucoadhesive polymer in the inner layer should be minimized or preferably absent.

Suitable anionic polymers or copolymers are as follows: cellulose glycolate (Duodcell®), cellulose acetate phthalate (CAP, "Celluosi acetas" as per European Pharmacopeia, cellulose acetate phthalate as per NF, or Aquateric®) cellulose acetate succinate (CAS), cellulose acetate trimellitate (CAT), hydroxy propyl methyl cellulose phthalate (HPMCP, HP50, HP55), hydroxy propyl methyl cellulose acetate succinate (HPMCAS-LF, -MF, -HF), polyvinyl acetate phthalate (PVAP or Sureteric®), vinyl acetate-vinylpyrrolidone copolymer (PVAc or Kollidon® VA64), a 9:1 vinyl acetate: crotonic acid copolymer (VAC:CRA or Kollicoat® VAC), and or shellac. These polymers and copolymers can often be formulated fully satisfactorily for pH-specific dissolution.

In a particularly preferred embodiment the film-applied outer coating essentially consists of a (meth)acrylate copolymer containing 5-60 wt-% of monomers with anionic groups, optionally mixed with pharmaceutically customary excipients, especially plasticizers. In comparison with the polymers mentioned at the outsets the anionic (meth)acrylate copolymers cited, in the context of the present invention, make it possible in many cases to fix the dissolution pH in an even more accurate and reproducible pH-specific manner. Furthermore, the handling and administration are usually regarded as more convenient here.

The (meth)acrylate copolymer used for the outer coating consists preferably of 40-95 wt-%, preferably 45-90 wt-% and especially 30- . . . wt-% of the product obtained by the free-radical polymerization of $C_1$-$C_4$ alkyl esters of acrylic acid or methacrylic acid, and can contain 5-60 wt-%, prefer-

| Mucoadhesive polymer | Mucoadhesivity $\eta_b$ at pH 5.5, mPa·s | Mucoadhesivity $\eta_b$ at pH 7.2, mPa·s | Water uptake at pH 5.5, % in 15 minutes | Water uptake at pH 6.0, % in 15 minutes | Water uptake at pH 7.2, % in 15 minutes |
|---|---|---|---|---|---|
| Chitosan | 220 | 0 | 140 | 320 | 320 |
| (Meth)acrylate copolymer* | 150 | 480 | 170 | 50 | 125 |
| Sodium alginate | 580 | 0 | 40 | 50 | 50 |
| sodium carboxymethyl cellulose | 300 | 250 | 55 | 50 | 50 |
| Cross-linked polyacrylic acid | 350 | 340 | 50 | 25 | 25 |

*(Meth)acrylate copolymer prepared from 30 wt-% of methyl methacrylate 70 wt-% of methacrylic acid ably 8-40 wt-% and especially 20-35 wt-% of (meth)acrylate monomers with an anionic group.

The sum of these components is generally 100 wt-%, but some other polymers may also be present in small amounts without changing or impairing the essential characteristics; this applies to 0-10 wt-%, e.g. 1-5 wt-%, of monomers that can be subjected to vinyl copolymerization, examples being hydroxyethyl methacrylate and hydroxyethyl acrylate The $C_1$-$C_4$ alkyl esters of acrylic acid and methacrylic acid mentioned above are especially methyl methacrylate, ethyl methacrylate, butyl methacrylate, methyl acrylate, ethyl acrylate and butyl acrylate.

The (meth)acrylate monomer with an anionic group can be e.g. acrylic acid, but methacrylic acid is preferred.

Also suitable are anionic (meth)acrylate copolymers composed of 40-60 wt-S of methacrylic acid and 60-40 wt-% of methyl methacrylate or 60-40 wt-% of ethyl acrylate of he type of Eudragit® L or Eudragit® 100-55.

Eudragit® L is a copolymer formed by 50 wt-% of methyl methacrylate and 50 wt-% of methacrylic acid Eudragit® L. L 30D is a dispersion containing 30 wt-% of Eudragit® L.

This (meth)acrylate copolymer is particularly suitable when a dissolution at pH 6.0-6.5 is required, which prevails in the jejunum Eudragit® L 100-55 is a copolymer formed by 50 wt-% of ethyl acrylate and 50 wt-% of methacrylic acid. Eudragit® L 30-55 is a dispersion containing 30 wt-% of Eudragit® L 130-55. This (meth)acrylate copolymer is particularly suitable when a dissolution at pH 5.5-6.0 is required which prevails in the duodenum.

Just as suitable are the anionic (meth)acrylate copolymers prepared from 20-40 wt-% of methacrylic acid and 80-60 wt-% of methyl methacrylate of the type of Eudragit® S. This (meth)acrylate copolymer is particularly suitable when a dissolution at pH 6.5-7.0 is required, which prevails in the jejunum and ileum.

Particularly suitable are the (meth)acrylate copolymers consisting of 10-30 wt-% of methyl methacrylate, 50-70 wt-% of methyl acrylate and 5-15 wt-% of methacrylic acid.

Eudragit® FS is a copolymer prepared from 25 wt-% of methyl methacrylate, 65 wt-% of methyl acrylate and 10 wt-% of methacrylic acid. Eudragit® FS 30 D is a dispersion containing 30 wt-% of Eudragit® FS. This (meth)acrylate copolymer is particularly suitable when a dissolution at pH 7.0-7.8 is required, which prevails in the ileum and colon.

A copolymer prepared from the following monomers is also suitable:
20-34 wt-% of methacrylic acid and/or acrylic acid
20-69 wt-% of methacrylate, and
0-40 wt-% of ethyl acrylate, and/or possibly
0-10 wt-% of other monomers that can be subjected to vinyl copolymerization.

However, the resulting copolymer must not have a glass transition temperature of over 60° C. as determined by ISO 11357-2 section 3.3.3. Owing to its good elongation at break, this (meth)acrylate copolymer is particularly suitable for compression of pellets into tablets.

Copolymers prepared from the following monomers are also suitable:
20-33 wt-% of methacrylic acid and/or acrylic acid
5-30 wt-% of methyl acrylate
20-40 wt-% of ethyl acrylate
more than 10 wt-% to 30 wt-% of butyl methacrylate, and possibly
0-10 wt-% of other monomers that can be subjected to vinyl copolymerization, with the total amount of the monomers being 100 wt-%.

However, this copolymer must have a mid-point glass transition temperature $T_{mg}$ of 55-70° C. as determined by ISO 11357-2 section 3.3.3. Owing to their good mechanical properties, these (meth)acrylate copolymers are particularly suitable for compression of pellets into tablets.

The above copolymer is particularly composed of the following free-radically polymerized units:
20-33 wt-%, preferably 25-32 wt-% and especially 28-31 wt-% of methacrylic acid or acrylic acid, but preferably methacrylic acids
5-30 t-%, preferably 10-28 wt-% and especially 15-25 wt-% of methyl acrylate,
20-40 wt-%, preferably 25-35 wt-% and especially 18-22 wt-% of ethyl acrylate, and
more than 10-30 wt-%, preferably 15-25 wt-% and especially 18-22 wt-% of butyl methacrylate.

The monomer composition is so chosen here that the glass transition temperature of the copolymer is 55-70° C., preferably 59-66° C. and especially 60-65° C.

Mixtures of the copolymers mentioned above can also be used for achieving special release profiles or release sites.

The glass transition temperature quoted here is the mid-point value ($T_{mg}$) specified in ISO 11357-2 section 3.3.3. This value is determined in an atmosphere of nitrogen, without any added plasticizer, at a residual monomer content (REMO) of less than 100 ppm, using a rate of heating of 10° C./minute.

The copolymer used preferably consists of 90, 95 or 99-100 wt-% (i.e. predominantly or exclusively) of the following monomers: methacrylic acid, methyl acrylate, ethyl acrylate and butyl methacrylate in the amounts ranges specified above.

However, the copolymer can without detriment to its essential qualities also contain small amounts (0-10 wt-% and e.g. 15 wt-%) of the following monomers, which are suitable for vinyl copolymerization: e.g. methyl methacrylate, butyl acrylate, hydroxyethyl methacrylate, vinyl-pyrrolidone, vinyl malonic acid, styrene, vinyl alcohol, vinyl acetate and/or their derivatives.

The copolymers mentioned above are mostly available commercially or can be obtained by mass, solution, bead or emulsion polymerization by the free-radical mechanism. Prior to use, they must be brought to the required particle-size range for the purposes of the invention by grinding, drying or spraying. This can be done by the simple comminution of the extruded and cooled granulate log or by hot fragmentation.

The use of powders can be particularly advantageous when other powders or liquids are admixed. Suitable devices for the preparation of powders are well known to the specialist in the field and include air-jet mills, disk mills and fan mills. Appropriate screening steps may also be included. A suitable mill for processing industrial quantities is for example the opposed jet mill Multi No. 4200, which is operated at an over pressure of about 6 bar.

Preparation of the Copolymer

The (meth)acrylate copolymers mentioned above can be prepared by the free-radical polymerization of the monomers (see e.g. EP 0 704,207 A2 and EP 0 704,208 A2). The copolymers are prepared by free-radical emulsion polymerization in an aqueous medium by a usual method, in the presence of preferably anionic emulsifiers, e.g. as described in DE-C 2,135,073.

Organic Solution

The (meth)acrylate copolymers mentioned above can be dissolved in an organic solvent to a concentration of e.g. 10-30 wt-%, suitable solvents used being e.g. acetone, isopropanol, ethanol or a mixture thereof, possibly with up to about 10 wt-% of water. However, aqueous dispersions are preferred.

Dispersions

The (meth)acrylate copolymers mentioned above can be prepared and used as emulsion polymers in the form of aqueous dispersions with a concentration of 10-50 wt-% and especially 20-40 wt-%. A solids content of 30 wt-% is preferred in the case of commercial preparations The partial neutralization of the methacrylic acid unfits is not necessary prior to use, but it can be carried out to an extent of e.g. 5 mole-% or 10 mole-% if it is considered desirable to stabilize or thicken the dispersion used for the coating agent. The weight-average particle size of the latex particles is generally 40-100 nanometers and preferably 50-70 nanometers, which ensures a viscosity of less than 1000 mPa·s, such values being favorable from the processing point of view.

In the case of a higher degree of neutralization such as for example 10-50 mole-%, or in the case of complete neutralization the copolymer can be converted into a dissolved state.

To prepare a solution of the anionic copolymer, a partial or complete neutralization of the acid groups is generally necessary. The anionic copolymer can be e.g. gradually stirred into water until a final concentration of 1-40 wt-% is reached, with partial or complete neutralization by the addition of a basic substance, such as for example sodium hydroxide, potassium hydroxide or ammonium hydroxide, or else an organic base, such as for example triethanolamine. It is also possible to use the copolymer in powder form, to which a base such as for example sodium hydroxide has been admixed already at the time of its preparation in order to achieve a full or partial neutralization, so that the powder already represents a fully or partly neutralized polymer. The pH of the solution is generally higher than 4 being in the range extending from 4 to about 7.

The dispersion can also be spray-dried or freeze-dried (lyophilized) in a conventional way and converted into a powder that car be redispersed (see e.g. EP A 0,252,326). Alternative methods are freeze-drying, coagulation and the removal of water in an extruder, followed by granulation (see e.g. EP A 0,683,028).

It has now been found surprisingly that copolymer dispersions prepared from spray-dried or freeze-dried and redispersed powders have a greater shear stability, which is particularly useful when they are sprayed on. This advantage is particularly pronounced when the copolymer is present in the dispersion in a partially neutralized form, having been neutralized to an extent of 2-10 mole-% (with respect to the acid groups in the copolymer. Partial neutralization by the addition of sodium hydroxide is preferred for this purpose. The presence of 0.1-2 wt-% of an anionic emulsifier, especially sodium lauryl sulfate, is preferred.

Thickness of the Layer

The outer coating preferably has a layer thickness of 20-200 μm and preferably 50-120 Sm.

ADVANTAGES OF THE INVENTION

The pharmaceutical form according to the invention is suitable for the targeted, effective release of active substances that only have a low or poorer solubility in water. The pharmaceutical form in question can be dosed accurately and is distributed well in the intestinal lumen. Its constituent active substance, which only has a low or poorer solubility in water, is well protected from physical or enzymatic inactivation and can be released at the defined site of action in such a way that a large part of it is absorbed by the body. Hence a smaller amount of the active substance is needed because only a small amount of it is lost. The danger of side effects is reduced overall by the targeted release. The site of action can be varied according to the therapeutic aim in question which makes for a better control of the time of absorption of the active substance by the body. Since it is for oral administration, the pharmaceutical form has a much better acceptance by the user, i.e. a better patient compliance than other forms of administration. In this way, numerous active substances with a low or poorer water-solubility become suitable for oral use for the first time, involving fewer risks in administration than, notably, drugs given by the parenteral route. The costs of administration can also be minimized, since there is no need for trained personnel here.

It is possible to achieve a faster drug release and at the same time a higher bioavailability by using a matrix system containing the mucoadhesive polymer in an amount that is twice and preferably 10-200 times as large as the amount of the active substance, in terms of weight-%.

Lipophilic Matrix

In a special embodiment of the present invention the active substance is embedded in a lipophilic matrix that has a melting point over 37° C., preferably over 40° C. and especially over 45° C. (as determined by differential scanning calorimetry or DSC), and the lipophilic matrix with the active substance is embedded in the matrix comprising the mucoadhesive polymer. The aim with the formulation in the lipophilic matrix is to improve the solubility and bioavailability of the active substance, especially when it has a low or very low solubility as defined in the German Pharmacopeia DAB 10.

The term "lipophilic matrix" is used in the invention in the sense of a substance or mixture of substances in which the active substance can be dissolved, suspended or emulsified. The substance or substances forming the lipophilic matrix are different both from the usual pharmaceutical excipients and from the mucoadhesive polymer. The substance or substances forming the lipophilic matrix preferably have a hydrophobic or even amphiphilic character. The lipophilic matrix could therefore be also described as an amphiphilic or a lipoid matrix.

The lipophilic matrix may consist of a single substance, e.g. a lipid, or of a mixture of substances, e.g. a mixture of lipids. In the case of mixtures, the DAB 10 water-solubility properties, the partition coefficients and the HLB values specified below are calculated from the arithmetic mean of the corresponding values of the substances and from their amounts in parts by weight. The substances used here must not be toxic.

The active substance and the substance or substances forming the lipophilic matrix differ from each other preferably in their water-solubility as defined in the German Pharmacopeia DAD 10 at most by +50% and preferably at most by ±25% in their distribution coefficient at most by ±60% and preferably at most by ±30% (as defined in Annexe V to EU Directive No. 67/548/EEC Point A.8, and in their HLE value at most by ±80% and preferably at most by ±40%, if the substances in question can be assigned an HLE value at all, as determined by Marszall's method. The closer the agreement between the active substance and the lipophilic matrix in at least one of these parameters, but preferably in two or all three of them, the better the solubility and bioavailability of the active substance contained in the pharmaceutical form.

Water-Solubility

The water-solubility of the active substance and the substance or substances forming the lipophilic matrix can be defined as described in DAD 10 German Pharmacopeia 10th ed. with 3rd suppl. 1994, published by Deutscher Apothekerverlag [=German Pharmacologic Publishing House], Stuttgart and by Govi Verlag, Frankfurt am Main, 2nd suppl. 1993, see Section IV "Allgemeine Vorschriften" [=General Methods] on pages 5 and 6, entitled "Löslichkeit und Lösungsmittell" [=Solubility and Solvents]; see also Ph. Eur. 4.07, 2004). The solubility is given here by the number of parts by volume of a solvent needed to dissolve 1 part by weight of the substance, such as a drug. "Low solubility" applies to substances that need 30-100 parts by volume of solvent to dissolve 1 part by weight of the substance or drug in question, while the terms "very low solubility", "sparingly soluble" and "difficultly soluble" apply to substances that need 100-1000 parts by volume of a solvent to dissolve 1 part by weight of the substance or drug in question.

Distribution Coefficient

The distribution or partition coefficients of the active substance and the substance or substances forming the lipophilic matrix can be determined as described in Annexe V to EU Directive No. 67/54/EEC Point (A.8, entitled "Verteilungskoeffizient" [=Distribution coefficient])

HLB Value

The HLB value was introduced by Griffin in 1950 as a measure of the hydrophilic or lipophilic nature of nonionic surfactants and can be determined experimentally by Marszall's phenol titration method [see *Parfümerie, Kosmetik* 60 (1979', pp. 444-448; see also *Römpp: Chemie-Lexikon,* 8th ed., 19833 p. 1750, and e.g. U.S. Pat. No. 4,795,643, Seth]. An HLB value (hydrophilic/lipophilic balance) can only be determined accurately for nonionic substances; in the case of anionic ones, it can be calculated but is almost always above or well above 14.

HLP values of the active substance and the substance or substances forming the lipophilic matrix can be determined by Marszall's method in most cases or taken from tables in pharmaceutical or chemical reference works or textbooks, or else—in the case of ionic substances—they can be calculated.

Active Substances in the Lipophilic Matrix

The pharmaceutical form preferably contains in its lipophilic matrix an active substance whose water-solubility according to DAB 10 is such that at least 30 and especially 30-100 or 100-1000 parts by volume of water are needed to dissolve 1 part by weight of the active substance in question. The preferred active substance therefore has a low or very low solubility in water according to the definition of the German Pharmacopeia DAB 10.

The active substance incorporated in the lipophilic matrix can be chosen from Classes II and IV of the Bio-Pharmaceutical Classification System (BCS) of Prof. Amidon. The active substances belonging to the various BCS Classes are known to the specialist in the field. The active substance incorporated in the lipophilic matrix can be chosen e.g. from the group of antiandrogens, antidepressants, antidiabetics, antirheumatics, glucocorticoids, cytostatics antimigraine drugs, neuroleptics, antibiotics, estrogens, vitamins, pyschopharmaceuticals, ACE inhibitors beta-blockers, calcium channel blockers, diuretics, cardiac glycosides, antiepileptics, diuretics/antiglaucoma agents, uricostatics, $H_2$ receptor blockers and virostatics.

The active substance incorporated in the lipophilic matrix can be e.g. bicalutamide, anastrozole, glimepiride, nilutamide, bromocriptine, ketotifen, letrozole, naratriptan, ganciclovir, orlistat, mesoprostol, granistron, pioglitazone, lamivudine, rosiglitazone, zidovudine, enalapril, atenolol, nadolol, felodipine, bepridil, furosemide, digoxin, digitoxin, carbamazepine, acetazolamide, allopurinol, cimetidine, ranitidine or oxcarbazepine.

Lipophilic Matrix/Mucoadhesive Polymer

Interactions that can take place between the lipophilic matrix and the mucoadhesive polymer are taken into account in one preferred embodiment. In order to avoid uncontrollable interactions, the substance or substances forming the lipophilic matrix and the mucoadhesive polymer should preferably have the same ionic character, i.e. they should both be fully or at least predominantly cationic or anionic. If these substances have opposite ionic characters, the mucoadhesive polymer should preferably be neutralized to an extent of at least 50% and more preferably to 100%, which can be achieved by the addition of an acid or base in the know way.

Substance or Substances Forming the Lipophilic Matrix 80-100 wt-%, preferably 90-100 wt-% and especially 100 wt-% of the lipophilic matrix preferably consists of a substance or a mixture of substances with a (mean) HLB value of 0-15 and preferably 2-10. The lipophilic matrix can contain 0-20 wt-% and preferably 0-10 wt-% of pharmaceutically customary excipients, especially stabilizers, thickeners or adsorbents. With particular preference there are no pharmaceutically customary excipients present.

The substance or substances forming the lipophilic-matrix can belong e.g. to the group of oils, fats, mono-, di- or triglycerides, fatty acids, fatty alcohols, especially $C_5$-$C_{20}$ fatty acid and/or a $C_1$-$C_{20}$ alcohol, including their salts, ether derivatives, ester derivatives or amide derivatives, phospholipids, lecithins, emulsifiers, lipoids, fat-soluble vitamins or surfactants.

The lipophilic matrix can contain e.g. one of the following lipid preparations:

Imwitor 308: glyceryl monocaprylate containing over 80% of the monoester

Imwitor 312: glyceryl monolaurate containing over 90% of the monoester

Imwitor 491: glyceryl monostearate ($C_{16}$+$C_{18}$) containing over 90% of the monoester Imwitor 900 P: glyceryl monostearate containing 40-55% of the monoester and 40-60% of $C_{18}$ compound Imwitor 900 K: glyceryl monostearate containing 40-55% of the monoester and 60-80% of $C_{18}$ compound Imwitor 742: medium-chain $C_8$ and $C_{10}$ glycerides containing 45-55% of monoesters Imwitor 928: partial glycerides formed with saturated $C_{10}$-$C_{18}$ fatty acids of plant origin, where the main component is $C_{12}$ compound, and the monoester content is 34-36%

$C_8$ and $C_{10}$ glycerides sodium caprylate, or sodium caprate.

The lipophilic matrix can e.g. contain one of the lipid preparations listed below. It car be formed either by one component or by a mixture of fats or lipids, such as mono-, di- and triglycerides of saturated and unsaturated fatty acids. Especially glyceryl stearates, glyceryl palmitates, glyceryl myristates, glyceryl palmitates/stearates, glyceryl laurates, glyceryl caprylates and glyceryl oleates. These esters are exemplified by Imwitor® 308, 312, 491, 742, 900, 023 and 988, and also by Gelucire® 44/14 and 50/13, Geleol Compritol E A-TO Dynasan 114, Softisan, Witepsol, Dynacet 212 and coconut oil.

Waxes, such as for example:

carnauba wax, beeswax, wool wax and glyceryl behenate

Oils, such as for example:

castor oil, sesame-seed oil, sunflower-seed oil, cottonseed oil, corn oil, almond oil, peanut oil, olive oil, coconut oil, carrot oil, wheat-germ oil and walnut oil Neutral oils, such as:
  isopropyl myristate, palmitate and stearate, as well as medium-chain triglycerides (Miglyol®)
Fatty alcohols, such as for example:
  stearyl alcohol, lauryl alcohol, cetyl alcohol, myristyl alcohol and glycerol formal
Fatty acid amides, such as for example:
  stearic acid amide, palmitic acid amide and lauric acid amide
Short-chain aliphatic and aromatic carboxylic acid esters, such as for example:
  dibutyl phthalate, diethyl sebacate, dibutyl sebacate, tributyl citrate, acetyl tributyl citrate and glyceryl triacetate
Long-chain aliphatic carboxylic acids, such as for example:
  stearic acid, palmitic acid, lauric acid, myristic acid, oleic acid, caprylic acid, linoleic acid, linolenic acid and arachidonic acid, plus e.g. their sodium, aluminum and magnesium salts.
Short-chain and medium-chain aliphatic carboxylic acids, such as for example: valeric acid, isovaleric acid, caproic acid, enanthic acid, caprylic acid, pelargonic acid and capric acid, plus e.g. their sodium, aluminum and magnesium salts
Water-in-oil emulsifiers, such as for example:
  cholesterol glyceryl monostearate, ethylene glycol monostearate, sorbitan monooleate (Span® 80)) sorbitan monopalmitate (Span®40) sorbitan monolaurate (Span® 20), sorbitan monostearate (Span® 60), sorbitan trioleate (Span® 85), sorbitan tristearate (Span® 65), sorbitan sesquioleate (Arlacel® 83) calcium, aluminum and magnesium stearate, polyoxyethylene sorbitan tristearate (Tween® 65), and polyoxyethylene sorbitan trioleate (Tween® 85).
Nonionic oil-in-water emulsifiers, such as for example:
Macrogol stearate 400 (Cremophor® A), Macrogol lauryl ethers polyethylene glycol 20 sorbitan monolaurate, polyethylene glycol 20 sorbitan monostearate, polyethylene glycol 20 sorbitan monopalmitate, polyethylene glycol 20 sorbitan monooleate, Macrogol 1500 glyceryl triricinoleate, Macroaol glyceryl hydroxystearate (Cremophor® RH), Macrogol 1000 glyceryl monolaurate, Macrogol 1000 glyceryl monostearate, Macrogol 1000 glyceryl monooleate, sucrose monostearate, Polysorbate 60 (Tween® 60)/polyoxyethylene monostearate (Myrj 49), Polysorbate 80 (Tween® 80) Polysorbate 40 (Tween® 40), Polysorbate 20 (Tween® 20), Poloxamer 407 (Lutrol® F 127), Poloxamer 188 (Lutrol® F 68), polyoxyethylene ricinoleate (Cremophor® EL), and polyoxyethylene-5-stearyl stearate
Ionic oil-in-water emulsifiers, such as for example:
cetyl stearyl sulfate (Lanette® E) sodium lauryl sulfate (Texapon® Z) sodium glycocholate, and hederagenin
Amphiphilic emulsifiers, such as for example:
phospholipids, lecithins, egg phosphatidyl choline (egg lecithin), soybean phosphatidyl choline (soybean lecithin), betaine, sulfobetaine, and ceramides (sphignomyelin)
Vitamins, such as for example:
retinol (vitamin A), cholecalciferol (vitamin D), α-tocopherol and α-tocopherol acetate (vitamin E) and their derivatives, and phylloquinone (vitamin K,
Galactolipids, such as for example:
monomalactosyl diacyl glycerol, digalactosyl diacyl glycerol and trigalactosyl diacyl glycerol Aromatic oils, such as for example:
  aniseed oil, citronellol, eucalyptus oil, fennel oil, camomile oil, cardamon oil, pine needle oil, caraway-seed oil, mountain pine oil, lavender oil, mint oil, mace oil, clove oil, peppermint oil, rosemary oil, and sage oil
Terpenes, such as for example:
  menthol, linalool, 1,4-cineol, pyrethrin, borneol, eudesmol, phytol, manool, azadirachtin and nimbin;

These substances can be selected specifically to set the desired solubility, partition coefficient (also known as the oil/water distribution coefficient) or HLB value, either singly or as a mixture.

The solubility of the active substance in the lipophilic matrix is preferably at least n0%, more preferably at least 20% and especially at least 50%.

The inner matrix layer a) can be present in the lipophilic matrix (with its active substance) in an amount of preferably 5-60 wt-% and especially 10-50 wt %.

The lipophilic matrix preferably contains at least 50 wt-% of glyceryl monocaprylate, up to 11 wt-% of sodium cholate, up to 10 wt-% of tocopherol succinate,
1-5 wt-% of an efflux pump inhibitor, if the active substance is a substrate for the P-glycoprotein efflux pump such as for example Solutol HS 15, and a triglyceride, especially tristearate, where the sum of the constituents is 100%. This lipophilic matrix can be directly incorporated into the mucoadhesive polymer, or it can be emulsified in water and then incorporated into the mucoadhesive polymer. In this second case, the aqueous phase may also contain a weak acid, such as for example citric acid.

Processes
Preparation of Prepellets and Pellets
The pelletizing can be carried out on nonpareilles (globules not containing any active substance yet), or pellets are made without a core.

The inner matrix layer is first made with or without the core. The resulting rounded layer, which is not coated yet, can be described as a prepellet.

Realization without a Neutral Core
The active substance is first dissolved or dispersed in the lipophilic matrix, or else it is mixed with it, using any of the common pharmaceutical methods. The lipophilic matrix is then emulsified, dispersed or dissolved in the aqueous medium, depending on its lipophilicity and on the chemical and physical properties of the matrix.

The aqueous medium can be just water or an aqueous medium containing acids, weak bases and salts, a 15% acetic acid solution being an example.

The resulting emulsion, dispersion or solution is used as a binder in the further processing of the mucoadhesive polymers in pellet form.

The ingredients of the inner matrix layer a), combined in this way, can be converted into rounded pellets (prepellets), as yet uncoated, of a given size, e. 50-1000 μm, by rotary agglomeration, precipitation, extrusion, granulation or spraying, especially by the technique of ultrasound-based fluidized-bed spraying. The advantage of this process is that the whole pellet volume is available for charging with the active substance.

The next section illustrates the realization in the exemplary case of rotary agglomeration in a fluidized-bed device (e.g. GPCG1 from Glatt) with a rotor attachment, which is charged with the mucoadhesive polymer powder and microcrystalline cellulose (MCC) powder. The latter can constitute up to 50% of the total amount of the powder. The airflow and the rotor are started up, and the binder is sprayed on. The aqueous phase causes the mucoadhesive polymer to swell, and at the same time it wets the microcrystalline cellulose powder, this effect being necessary for the formation of prepellets by the centrifugal force of the rotor attachment. The microcrystalline cellulose also makes the material easier to shape, leading to a better control of the physical properties of the prepellets e.g. their density, shape and resistance to abrasion). While the prepellets are being formed, the lipophilic part of the binder is distributed over the powder particles' surfaces and so remains uniformly distributed or embedded in the pellets in the form of micro-domains.

Realization with a Neutral Core

In this variant, the lipophilic and/or amphiphilic solution of the active substance is emulsified, dispersed or dissolved in an aqueous medium that already contains the mucoadhesive polymer in the form of a dispersion or solution. This emulsion, dispersion or solution is then sprayed on a neutral core in the customary fluidized-bed plant in order to form a layer over it. To ensure that the mixture can be satisfactorily sprayed, it must usually have a low viscosity. For this reason, it may be convenient to use the mucoadhesive polymer in a comparatively low concentration of for example from X wt-% to at most 10 wt-% and preferably 2-5 wt-%. The addition of a detergent such as Tween in a concentration of 0.1-20 wt-% and preferably 0.5-10 wt-% may also help reduce the surface tension.

The active substance can be accompanied by further pharmaceutical excipients: binders, such as cellulose, cellulose derivatives, polyvinylpyrrolidone (PVP), humectants, disintegration promoters, glidants, disintegrants, (methacrylates, starches, starch derivatives, sugar, solubilizers or others.

Appropriate coating methods are described e.g. in a book by Bauer, Lehmann, Osterwald and Rothgang entitled "Überzogene Arzneiformen" [=Coated Pharmaceutical Preparations], published by Wissenschafliche Verlagsgesellschaft mbH in Stuttgart (see pages 165-196 in Chapter 7 there).

The details are known to the specialist in the field from various textbooks, such as:

R. Voigt: "Lehrbuch der pharmazeutischen Technologie" [=Textbook of Pharmaceutical Technology], published by Verlag Chemie, in Weinheim—Beerfield Beach (Florida) and Basle, 1984

H. Sucker, P. Fuchs and P. Speiser: "Pharmazeutische Technologie" [=Pharmaceutical Technology], published by Georp Thieme Verlag, Stuttgart, 1991 (see especially Chapters 15 and 16 on pages 626-642)

A. R. Gennaro (ed.): "Remington's Pharmaceutical Sciences", published by Mack Publishing Co., Easton (Pa), 1985 (see Chapter 88 on pages 1567-1573), and P. H. List: "Arzneiformenlehre" [=Pharmaceutical Dosage Forms], published by Wissenschaftliche Verlagsgesellschaft mbH, Stuttgart, 1982.

After preparation of the inner matrix cores (or the prepellets), they are given the outer coatings to produce finished pellets, preferably again by spraying. The pellets are prepared by the coat-spraying method, using an organic solution or preferably an aqueous dispersion. The important thing here is to produce a uniform coating that is free of pores Top Coat The pellets can also be given in addition a pigmented coating but this should not alter their dissolution pH. Suitable coating agents are pigmented hydroxypropyl methyl celluloses and other polymers that either dissolve in water or rapidly disintegrate in it Pharmaceutically Customary Excipients The formulations according to the invention can also be admixed during their preparation with customary excipients and/or additives. All these substances must of course be toxicologically harmless and in particular involve no risks to the patients when included in pharmaceutical preparations The specialist in the field will know which of the customary additives to use when coating pharmaceutical preparations and in what quantities. Customary additives may be plasticizers, separating agents, pigments, stabilizers, antioxidants, pore formers, penetration improvers, gloss enhancers (glossants) aroma agents, detergents lubricants or flavors. These substances facilitate processing and should ensure a reliable and reproducible production process and a satisfactory long-term stability. Alternatively, they can also exert some additional advantageous effects in the product. They are added to the polymer preparations prior to processing and can affect the permeability of the coatings, which can be used if desired as an additional control parameter.

Separating Agents

Separating agents, release agents or antiadherents are generally lipophilic and are usually incorporated into the spray suspensions. They prevent the agglomeration of the cores during the film coating process. The preferred separating agents are talc, magnesium stearate, calcium stearate, ground silica, kaolin or nonionic emulsifiers with an HLB value of 3-8. The separating agent is normally used in the coating and binding agents according to the invention in an amount of 0.5-100 wt-%, calculated on the weight of the copolymer.

Pigments

The pigments are not compatible with the coating agent especially when dispersion destabilization, coagulation, demixing or similarly undesired events occur when they are added directly to the (meth)acrylate copolymer dispersion, e.g. by stirring them into the latter in the usual amounts of 20-400 wt-%, calculated on the dry weight of the (meth)acrylate copolymer. The pigments used must of course not be toxic either, and must be suitable for pharmaceutical purposes. See in this connection also the publication of the Deutsche Forschungsgemeinschaft [=German Research Association] entitled "Farbstoffe für Lebensmittel" [=Food Dyes], published by Harald Boldt Verlag K G, Boppart, 1978, as well as the article Deutsche Lebensmiittelrundschau, 74, No. 4 (1978), page 156, and the German Pharmaceutical Dyes Act [="Arzneimittelfarbstoffverordnung"—AmFarbV] dated Aug. 25, 1980.

Pigments that are incompatible with the coating agent may include aluminum oxide pigments. Incompatible pigments include yellow orange, cochineal red lacquer, colored pigments based on aluminum oxide and/or azo dyes, sulfonic acid dyes, yellow orange S (E110, C.I. 159853, FD&C Yellow 6), indigo carmine (E132, C.I. 73015, FD&C Blue 21, tartrazine (E102, C.I. 19140, FD&C Yellow 53, ponceau 4R (E125, C.I. 16255, FD&C Cochineal Red A), quinoline yellow (E104, C.I. 47005, FD&C Yellow 10), erythrosine (E27, C.I. 45430, FD&C Red 3), azorubine (E122, C.I. 14720, FD&C Carmoisine), amaranth (E123, C.I. 16185, FD&C Red 2), and acid brilliant green (E142, C.I. 44090, FD&C Green S).

The above E numbers of the pigments listed are those established by the European Union [see in this connection also the publication of the Deutsche Forschungsgemeinschaft [=German Research Association] entitled "Farbstoffe für Lebensmittel" [=Food Dyes], published by Harald Foldt Verlag K G, Boppart, 1978, as well as the article in Deutsche Lebensmiittelrundschau, 74, No. 4 (1978), page 156, and the German Pharmaceutical Dyes Act [="Arzneimittelfarbstoffverordnung"—AmFarbV] dated Aug. 25, 1980]. The FD&C numbers given above are those used in Food, Drugs and Cosmetics authorization by the US Food and Drug Administration (FDA), described in: U.S. Food and Drug Administration, Center for Food Safety and Applied Nutrition, Office of Cosmetics and Colors: Code of Federal Regulations—Title 21: Color Additive Regulations, part 82, Listing of Certified Provisionally Listed Colors and Specifications (CFR 21, part 82).

Plasticizers

Plasticizers can also be added, the usual amounts being 0-50 wt-%, preferably 2-20 wt-% and especially 5-10 wt-%.

Plasticizers affect the performance of the polymer layer differently, according to whether they are lipophilic or hydrophilic, and according to the amount in which they are added. Owing to their physical interaction with the polymer, they lower the glass transition temperature and promote film formation, depending on the amount used Suitable substances generally have a molecular weight of 100-20,000 and contain one or more hydrophilic groups in the molecule, e.g. hydroxyl, ester or amino groups.

Suitable plasticizers are exemplified by alkyl citrates, glycerol esters, alkyl phthalates, alkyl sebacates, sucrose esters, sorbitan esters, diethyl sebacate, dibutyl sebacate and polyethylene glycols 200-12,000. The preferred plasticizers are triethyl citrate (TEC) and acetyl triethyl citrate (ATEC). Esters such as citrates, phthalates and sebacates, which are generally liquid at room temperature, as well as castor oil can also be mentioned here. Esters of citric acid and of sebacic acid are used by preference.

The plasticizer can be introduced into the formulation in a known way, directly, in aqueous solution or after a thermal pretreatment of the mixture. Mixtures of plasticizers can also be used.

Preparation of Multiparticle Pharmaceutical Forms

The coated pellets that contain the active substance car be converted into multiparticle pharmaceutical forms in a usual way, with the inclusion of customary pharmaceutical excipients. The multiparticle forms can be especially pellet-containing tablets, minitablets, capsules, sachets or reconstitutable powders and are so formulated that their constituent pellets are released in the pH range of the stomach. Owing to the multiparticle form, the pharmaceutical product can be dosed accurately, and the pellets are well distributed in the intestinal lumen. The multiparticle pharmaceutical form according to the present invention can also contain different types of pellets, with different active substances and/or different pellet constructions.

Compressed Tablets

The preparation of multiparticle pharmaceutical forms by compressing a pharmaceutically customary binder with particles that contain the active substance is described e.g. in an article by Beckert et al., entitled "Compression of enteric-coated pellets to disintegrating tablets", published in *International Journal or Pharmaceutics,* 143, (1996), pp. 13-23, and in WO 96/01624.

The pellets containing the active substance are given a film coating typically in fluidized-bed plant. Formula examples are given in this patent application. The film-formers are customarily mixed with plasticizers and separating agents, with the aid of a suitable process. The film-formers can be present here as a solution or suspension. The additives for the film formation can also be in the dissolved or suspended form. Organic or aqueous solvents or dispersing agents can be employed. Stabilizers can also be incorporated in order to stabilize the dispersion, examples being Tween 80 and other suitable emulsifiers or stabilizers.

The separating agents (release agents; antiadherents) used are exemplified by glyceryl monostearate, other suitable fatty acid derivatives, silicas and talc. Examples of plasticizers are propylene glycol, phthalates, polyethylene glycols, sebacates or citrates, and also other substances mentioned in the literature.

A separating layer can be applied between the layer containing the active substance and the copolymer layer that dissolves in the intestines, the aim being to separate the active substance and the coating material, so as to prevent any interaction between them. This separating layer can be made of inert film-formers [e.g. HPMC, HPC or (meth)acrylic acid copolymers] or e.g. talc or another suitable pharmaceutical substance. Combinations of film-formers and talc or similar substances can also be used. A separating layer made from partially or fully neutralized (meth)acrylate copolymer dispersions can also be applied.

A separating layer can also be introduced between the inner layer a) and the film-applied outer layer D. This separating layer can also be made of the same mucoadhesive polymer as the one in the underlying layer, or else it is made of a different mucoadhesive polymer. This can prevent any interaction or incompatibility between the active substance or the mucoadhesive polymer on the one hand and the film-forming (meth)acrylate copolymer layer on the other hand.

To prepare a mixture for producing tablets from coated particles, the pellets are mixed with suitable binders for tabletting, possibly with the addition of disintegrants and lubricants if necessary. The mixing can be carried out in suitable equipment. Mixers that damage the coated particles, such as plowshare mixers are unsuitable. A special sequence may have to be observed when admixing the various additives to the coated particles, in order to obtain a suitable short disintegration time. By premixing the coated particles with magnesium stearate, a lubricant or mold release agent, the surface of the particles can be rendered hydrophobic, thereby preventing their agglomeration.

Suitable tabletting mixtures normally contain 3-15 wt-% of a disintegrant, for example Kollidon CL, and e.g. 0.1-1 wt-% of a lubricant and mold release agent, such as magnesium stearate. The amount of binder used depends on the required proportion of coated particles. Typical binders include for example Cellactose®, microcrystalline cellulose, calcium phosphate, Ludipress®, lactose or other suitable sugars, calcium sulfates or starch derivatives. Substances with a low bulk density are preferred.

Typical disintegrants are cross-linked starch derivatives or cross-linked cellulose derivatives, and also cross-linked polyvinylpyrrolidone, but other cellulose derivatives can also be used. If the binder is correctly chosen, no disintegrant may be needed.

Typical lubricants and mold release agents are magnesium stearates or other suitable salts of fatty acids, or substances mentioned in the literature for this purpose (e.g. lauric acid, calcium stearate, talc, etc.). It is possible that no lubricant and mold release agent are needed if a correct formulation and a suitable machine (for example a tabletting press with external lubrication) are employed.

The mixture may optionally have been admixed with a free-flow improving agent (e.g. highly disperse silica derivatives, talc, etc.).

Tabletting can be carried out on usual tablet presses, eccentric or rotary tabletting presses, using a compressive force of 5-40 kN and preferably 10-20 kN The tabletting presses may be fitted with an external lubricating system. Special die filling systems may be used to avoid the filling of the dies of the machine with the aid of stirrer arms.

Other Multiparticle Pharmaceutical Form

As an alternative to the production of compressed tablets or minitablets, the coated pellets with their active substance can be processed into other oral multiparticle pharmaceutical forms. For example, the coated pellets can be introduced into capsules—gelatine capsules, for example—or formulated as sachets or reconstitutable powders.

Process for Making a Multiparticle Pharmaceutical Form

The present invention also relates to a process for the preparation of a multiparticle pharmaceutical form, comprising the following steps:
a) the lipophilic matrix containing the active substance is prepared by suspending and/or dissolving the active substance with the substance or substances forming the lipophilic matrix, possibly together with other pharmaceutically customary excipients, by intense mixing or melting of the constituents,
b) prepellets (pellet cores) are prepared by spraying the mucoadhesive polymer, mixed with the lipophilic matrix that contains the active substance, onto a core, or by rotary agglomeration, precipitation or spraying without any core,
c) pellets are produced by spraying the prepellets obtained in step b), from a dispersion or organic solution, with a coating of the anionic polymer or copolymer, optionally containing admixtures of pharmaceutically customary excipients, especially plasticizers and separating agents,
d) a multiparticle pharmaceutical form is prepared by introducing or incorporating the pellets obtained in step c) in a conventional way, possibly using pharmaceutically customary excipients, especially by processing the composition into pellet-containing tablets, minitablets, capsules, sachets or reconstitutable powders.

Preferred Process

The process steps a) and b) are preferably carried out as follows:
a) the inner matrix layer is made by preparing an emulsion, dispersion or solution of the active substance with the one or more substances for the lipophilic matrix and possibly with other pharmaceutically customary excipients, by intensely mixing the constituents in water and preparing an oil-in-water system with an average particle size of at most 60 µm and preferably at most 20 µm,
b) prepellets are prepared by spraying the oil-in-water system obtained in step a) onto the mucoadhesive polymer, which may also contain some pharmaceutically customary excipients, where the ingredients are present in the form of a micron zed powder with an average grain size for example of 10-100 µm, by rotary agglomeration, extrusion or granulation

ADVANTAGES OF THE INVENTION

The pharmaceutical form according to the invention is suitable for the targeted, efficient release of low-solubility active substances other than peptides and proteins and their derivatives or conjugates. The pharmaceutical form features a high dosing accuracy and is well distributed in the intestinal lumen. The active substance in it is extensively protected from physical, chemical or enzymatic inactivation and can be released at the defined site of action in such a way that a large proportion of it can be absorbed by the body. Therefore, a smaller amount of the active substance is needed because only a small amount of it is lost. The danger of side effects is largely reduced by the targeted release. The site of action can be varied according to the therapeutic aim. The time for the absorption of the active substance can therefore be controlled better. Since the product in question is a form for oral administration, it has, overall, a better acceptance by the patients, i.e. a better patient compliance, than other dosage forms. As a result, numerous low-solubility active substances now become suitable for oral administration for the first time, involving less risk on administration than especially in the case of parenteral administration. The costs can also be kept low, since there is no need for trained personnel for the administration.

An accelerated release coupled with a simultaneous increase in bioavailability can be obtained with matrix systems in which the amount of the mucoadhesive poly-mer is preferably twice as much and especially 10-200 times as much as the amount of the active substance in terms of weight-%.

EXAMPLES

Examples of Embodiments with a Lipophilic Matrix Containing an Active Substances Example 1

Zidovudine was used here, whose water solubility, as defined in German Pharmacopeia DAB 10, is such that at least 50 parts of water are needed to dissolve 1 part of the active substances which corresponds to a water solubility of 20 g/liter.

a) Preparation of the Lipophilic Phase 150 g of Imwitor 312 (melting range: 55-60° C.) were melted on a water bath at 65° C., and 75 g of Poloxamer 407 (Lutrol F127, melting range: 50-55° C.) were slowly stirred into the resulting melt. The water bath was cooled to 52° C., and 12.5 g of tocopherol acetate and 5 g of sodium glycocholate were added, with stirring. Thus the temperature of the bath could be reduced here by a further 5° C. without the fat solidifying out again. The resulting lipophilic matrix therefore had a melting range of 38-41° C. and the water solubility according to German Pharmacopeia DAB 10, calculated from the individual components, was at least 40 parts of water for 1 part of the lipophilic matrix, corresponding to a water solubility of 25 g/liter. 500 g of zidovudine were added to this solution, with stirring.

b) Preparation of a Dispersion 1500 ml of distilled water were first heated to 45° C., and 30 g (2%) of sodium caprate were added as an emulsifier. This solution was then adjusted to a pH of about 7 with citric acid, and the lipophilic phase was introduced into this solution, with energetic stirring to produce a dispersion. The dispersion process was stopped when no lipophilic particles with a size greater than 50-60 µm could be seen under the microscope.

c) Preparation of Mucoadhesive Cores 700 g of sodium alginate in powder form, 285 g of microcrystalline cellulose and 15 g of citric acid were mixed in a GPCG1 apparatus, fitted with a rotor attachment. The dispersion described in b) was sprayed on as a binder in a rotary agglomeration process using a spraying rate of about 90 g/minute.

The rotor was operated at a speed of 1700-1800 rpm, the inlet air was introduced at a rate of 42 m$^3$/h, and the air temperature was adjusted to 30° C.

Under these conditions, mucoadhesive cores measuring 250-600 µm could be produced in a yield of up to 80%.

The therapeutic dose of 250 mg was present in 886 ma of pellet cores.

d) Preparation of Coated Pellets

The pellet cores from c) were coated with Eudragit® FS 30 D in a customary fluidized-bed process (Eudragit® FS 30 D is a 30% aqueous dispersion of Eudragit® FS, which is a copolymer prepared from 65 wt-% of methyl acrylate, 25 wt-% of methyl methacrylate and 10 wt-% of methacrylic acid) The polymer layer amounted to 40 wt-% of the weight of the cores. The dispersion or suspension used for coating had the following composition:

| | |
|---|---|
| Eudragit ® FS 30 D | 44.65% |
| Triethyl citrate | 0.67% |
| Polysorbate 80 | 0.26% |
| Glyceryl monostearate | 0.67% |
| Water | 53.75%. |

The pellets obtained in this way could be compressed into tablets using customary pharmaceutical processes and excipients, or else they could be introduced into capsules Example 2

Rosiglitazone was used here, whose water solubility according to German Pharmacopeia DAB 10 is such that at least 1000 parts of water are needed to dissolve 1 part of the active substance, which corresponds to a water solubility of 1 g/liter.

a) Preparation of the Lipophilic Phase 13 g of Imwitor 312 (melting range: 55-60° C.) and 4 g of Poloxamer 407 (Lutrol F127, melting range. 50-55° C.) were melted on a water bath at 65° C., after which 1 g of caprylic acid, 1 g of sodium caprylate and 1 g of tocopherol acetate were added, with stirring. The resulting lipophilic matrix therefore had a melting range of 40-48° C., and the water solubility according to German Pharmacopeia DAB 10, calculated from the individual components, was at least 700 parts of water for 1 part of the lipophilic matrix, corresponding to a water solubility of 1.5 g/liter. After cooling of the solution to 45° C., 2.9 g of rosiglitazone were added to the lipophilic phase, with rapid stirring, and the mixture was cooled.

b) Preparation of a Mucoadhesive Dispersion 20 g of chitosan were dispersed in 1000 g of water, and 20 g of citric acid were then added with very rapid stirring. This gave a clear yellowish viscous solution, to which 2 g of sodium dodecanate were added, with rapid stirring. The mixture was then stirred for another hour.

c) Preparation of a Suspension for Spraying

The dispersion prepared in a) was dispersed for at least 10 minutes with the chitosan citrate dispersion from b) using an Ultraturrax mixer at a speed of 20,000 rpm, with further cooling to 10° C. on an ice bath. The dispersion process was stopped when no lipophilic particles with a size greater than 50-60 µm Gould be seen under the microscope.

c) Preparation of Mucoadhesive Cores

The suspension from c) was sprayed on and applied to 250 g of neutral pellets having a size of 400-600 µm in a GPCGL apparatus from Glatt, using a spraying rate of 10-12 g/min/kg and an inlet air temperature of 30° C. The inlet air was introduced at a rate of 45-50 m³/h. The yield here was 90%. The therapeutic dose of 8 mg was present in 179 mg of pellet cores.

d) Preparation of Coated Pellets

The pellets obtained above were coated with Eudragit® L12.5 in a customary fluidized-bed process. The polymer layer amounted to 40% of the weight of the cores. The suspension used for coating had the following composition:

| | |
|---|---|
| Eudragit ® L12.5 | 53.3% |
| Triethyl citrate | 1.33% |
| Isopropanol | 38.3% |
| Talc | 2.0% |
| Water | 5.0%. |

The pellets obtained in this way could be compressed into tablets using usual pharmaceutical processes and excipients, or else they could be introduced into capsules.

Example 3

Oxcarbazepine was used here, whose water solubility according to German Pharmacopeia DAB 10 is such that at least 10,000 parts of water are needed to dissolve 1 part of the active substances which corresponds to a water solubility of 0.1 g/liter.

a) Preparation of the Lipophilic Phase 200 g of Imwitor 312 (melting range: 55-60° C.) and 400 g of Dynasan 114 (melting rage: 55-58° C.) were melted with 30 g of tocopherol acetate at 65° C. and Introduced into a Bohle granulator, after which 200 of sodium caprylate were added, with stirring. The mixture was cooled to 45° C. and 940 g of oxcarbazepine were dissolved in it. The resulting lipophilic matrix therefore had a melting range of 39-46° C., and the water solubility according to German Pharmacopeia DAB 10, calculated from the individual components, was such that at least 7000 parts of water were needed to dissolve 1 part of the lipophilic matrix. The lipophilic matrix was ground to a particle size of less than 50 µm, with cooling.

b) Preparation of a Buffer Solution 1 g of sodium citrate and 1 g of citric acid were dissolved in 500 g of water, and 0.5 g of sodium cholate were added to the solution, with rapid stirring.

c) Granulation

The ground lipophilic matrix that contained the active substance, from a), was mixed with 1500 g of Blanose 7LF in a granulator Granulation was then continued with the aqueous buffer solution from b), and the resulting particles, measuring 0.2-0.5 mm, were rounded off in a spheronizer. The moist cores thus obtained were lightly dried at 30-25° C. in a fluidized-bed dryer. The therapeutic dose of 300 mg was present in 837 mg of pellet cores.

d) Preparation of Coated Pellets

The resultant cores from c) were coated with Eudragit® FS 30D in a customary fluidized-bed process. The polymer layer amounted to 40 wt-% of the weight of the cores. The dispersion or suspension used for coating had the following composition:

| | |
|---|---|
| Eudragit ® FS 30 D | 44.65% |
| Triethyl citrate | 0.67% |
| Polysorbate 80 | 0.26% |
| Glyceryl monostearate | 0.67% |
| Water | 53.75%. |

The pellets obtained in this way could be compressed into tablets using usual pharmaceutical processes and excipients, or else they could be introduced into capsules.

The invention claimed is:

1. A composition suitable for oral administration comprising a casing that disintegrates in a gastric pH range and that contains
pellets, particles, granules or agglomerates that have a mean diameter ranging between 50 and 2,500 μm and comprising:
a) an inner matrix layer comprising
an active substance other than a peptide, protein, peptide or protein derivative, or peptide or protein conjugate,
a lipophilic matrix with a melting point of over 37° C.; and
a mucoadhesive polymer; and
b) a film-applied outer coating, consisting essentially of an anionic polymer or copolymer, and, optionally, one or more pharmaceutically customary excipients,
wherein the active substance in the inner matrix layer has a water-solubility as defined in the German Pharmacopeia DAB 10 of at least 30 parts by volume of water for 1 part by weight of the active substance,
wherein the lipophilic matrix with its active substance is embedded in a matrix made from the mucoadhesive polymer used jointly with an acid or a buffer system which is present in the matrix or in or on a core to which the matrix is applied, which matrix comprises a chitosan and is adjusted to pH 5.0-5.5 by means of the acid or a buffer system, and is combined with a film-applied outer coating which begins to dissolve in the range of pH 6.0 to 8.0.

2. The composition of claim 1, wherein the active substance and the substance or substances forming the lipophilic matrix do not differ from each other in their water-solubility as defined in the German Pharmacopeia DAB 10 by more than ±50%, in their distribution coefficient defined in Annexe V to EU Directive No. 67/548/EEC Point A.8 by more than ±60%, and/or in their HLB value as measured by Marszall's method by more than ±80%.

3. The composition of claim 1, wherein the mucoadhesive polymer and the substance or substances forming the lipophilic matrix either have the same ionic character, or—if they have opposite ionic characters—the mucoadhesive polymer is present in a form neutralized to an extent of at least 50%.

4. The composition of claim 1, wherein 80-100 wt-% of the lipophilic matrix is formed by a substance with an HLB value of 0-15 or by a mixture of substances with a mean HLB value of 0-15, and can contain 0-20 wt-% of pharmaceutically customary excipients, especially stabilizers, thickeners or adsorbents.

5. The composition of claim 1, wherein the substance or substances forming the lipophilic matrix are selected from the group consisting of oils, fats, mono-, di- or triglycerides, fatty acids, fatty alcohols, including their salts, ether derivatives, ester derivatives or amide derivatives, phospholipids, lecithins, emulsifiers, lipoids, fat-soluble vitamins and surfactants.

6. The composition of claim 1, wherein the lipophilic matrix contains one of the following lipid preparations: Imwitor 308 (glyceryl monocaprylate containing over 80% of the monoester), Imwitor 312 (glyceryl monolaurate containing over 90% of the monoester), Imwitor 491 [glyceryl monostearate ($C_{16}$+$C_{18}$) containing over 90% of the monoesters], Imwitor 900 P (glyceryl monostearate containing 40-55% of the monoester and 40-60% of $C_{18}$ compound), Imwitor 900 K (glyceryl monostearate containing 40-55% of the monoester and 60-80% of $C_{18}$ compound), Imwitor 742 (medium-chain $C_8$ and $C_{10}$ glycerides containing 45-55% of monoesters), Imwitor 928 (partial glycerides formed with saturated $C_{10}$-$C_{18}$ fatty acids of plant origin, where the main component is $C_{12}$ compound and the monoester content is 34-36%), $C_8$ and $C_{10}$ glycerides, sodium caprylate or sodium caprate.

7. The composition of claim 1, wherein the active substance is soluble in the lipophilic matrix to an extent of at least 10%.

8. The composition of claim 1, wherein the amount of the inner matrix layer a) in the lipophilic matrix that contains the active substance is 5-60 wt-%.

9. The composition of claim 1, wherein the casing that disintegrates in the gastric pH range is a capsule, a tablet, a reconstitutable powder formulation, or a sachet.

10. The composition of claim 1, wherein the properties of the outer coating are adjusted by the appropriate choice of the anionic polymer or copolymer and formulation or of its excipients with and of its layer thickness, in such a way that it—the outer coating—dissolves in the gut at a pH of 4.0-8.0 within 10-60 minutes, so that the lipophilic matrix embedded—with its active substance—in the mucoadhesive matrix layer is exposed, can bind to the intestinal mucosa and can release the active substance there; the mucoadhesive polymer is so chosen that, when the pH is within ±0.5 pH units from the pH value at which the outer coating begins to dissolve, it possesses a mucoadhesive action $\eta_b$ of 150-1000 mPa·sec and a water absorption of 10-750% in 15 minutes, and the active substance constitutes at most 90 wt-% of the lipophilic matrix.

11. The composition of claim 1, wherein the film-applied outer coating is cellulose glycolate, cellulose acetate phthalate (CAP, cellulose acetate succinate (CAS), cellulose acetate trimellitate (CAT), hydroxy propyl methyl cellulose phthalate (HPMCP, HP50, HP55), hydroxy propyl methyl cellulose acetate succinate (HPMCAS-LF, -MF -HF), polyvinyl acetate phthalate (PVAP), vinyl acetate-vinylpyrrolidone copolymer (PVAc), a 9:1 vinyl acetate:crotonic acid copolymer (VAC:CRA) and/or shellac.

12. The composition of claim 1, wherein the film-applied outer coating consists of a (meth)acrylate copolymer containing 5-60 wt-% of monomers with anionic groups.

13. The composition of claim 1, the layer thickness of the outer coating is from 20 to 200 μm.

14. The composition of claim 1, the inner layer a) contains an efflux pump inhibitor and/or a penetration promoting agent.

15. The composition of claim 1, wherein the mucoadhesive polymer further comprises a (meth)acrylate copolymer consisting of 20-40 wt-% of methyl methacrylate and 60-80 wt-% of methacrylic acid, a cellulose, a cross-linked or non-cross-linked polyacrylic acid, a lectin, a sodium alginate and/or a pectin.

16. The composition of claim 1, wherein there is a separating layer applied between the inner layer a) and the film-applied outer coating layer b).

17. The composition of claim 1, wherein the active substance formulated in the lipophilic matrix is
selected from the group consisting of Classes II and IV of the Bio-Pharmaceutical Classification System (BCS) of Prof. Amidon; and/or
selected from the group consisting of antiandrogens, antidepressants, antidiabetics, antirheumatics, glucocorticoids, cytostatics, antimigraine drugs, neuroleptics, antibiotics, estrogens, vitamins, pyschopharmaceuticals, ACE inhibitors, beta-blockers, calcium channel blockers, diuretics, cardiac glycosides, antiepileptics, diuretics/antiglaucoma agents, uricostatics, $H_2$ receptor blockers and virostatics.

18. The composition of claim 1, wherein the active substance formulated in the lipophilic matrix is bicalutamide, anastrozole, glimepiride, nilutamide, bromocriptine, ketotifen, letrozole, naratriptan, ganciclovir, orlistat, mesoprostol, granisetron, pioglitazone, lamivudine, rosiglitazone, zidovudine, enalapril, atenolol, nadolol, felodipine, bepridil, furosemide, digoxin, digitoxin, carbamazepine, acetazolamide, allopurinol, cimetidine, ranitidine or oxcarbazepine.

19. A process for preparing the composition of claim 1 comprising:
  (i) suspending and/or dissolving the active substance in the components that form the lipophilic matrix having a melting point of over 37° C., optionally in the presence of one or more pharmaceutically customary excipients, by mixing or melting to form a lipophilic matrix containing the active substance, wherein the active substance is other than a peptide or a protein and their derivatives or conjugates;
  (ii) mixing the lipophilic substance containing the active substance with the mucoadhesive polymer(s) and spraying the mixture onto a core, or subjecting the mixture to rotary agglomeration, precipitation or spraying without any core, to form prepellets, wherein the mucoadhesive polymer(s) comprise a chitosan and have been adjusted to pH 5.0-5.5 by means of the acid or a buffer system;
  (iii) spraying the prepellets obtained in step (ii) from a dispersion or organic solution with an outer coating of the anionic polymer or copolymer which begins to dissolve in the range of pH 6.0 to 8.0 and which coating may optionally contain one or more plasticizers, separating agents, or other pharmaceutically customary excipients to produce pellets, particles, granules or agglomerates having a mean diameter of 50 to 2,500 µm;
  (iv) incorporating the pellets, particles, granules or agglomerates obtained in step (iii) into a multiparticle pharmaceutical form.

20. The process of claim 19, wherein steps (i) and (ii) are carried out as follows:
  (i) the inner matrix layer is made by preparing an emulsion, dispersion or solution of the active substance with the one or more substances for the lipophilic matrix and possibly with other pharmaceutically customary excipients, by intensely mixing the constituents in water and preparing an oil-in-water system with an average particle size of at most 60 µm,
  (ii) prepellets are prepared by spraying the oil-in-water system obtained in step a) onto the mucoadhesive polymer, which may also contain admixtures of pharmaceutically customary excipients, where the ingredients are present in the form of a micronized powder, by rotary agglomeration, extrusion or granulation.

21. A composition comprising a casing, which disintegrates in the gastric pH range, and which contains numerous pellets, particles, granules or agglomerates with a mean diameter of 50-2,500 µm; wherein said pellets, particles, granules or agglomerates consist essentially of:
  a) an inner matrix layer comprising an active substance other than a peptide or a protein and their derivatives or conjugates; a lipophilic matrix with a melting point of over 37° C.; and a mucoadhesive polymer,
  b) a film-applied outer coating consisting essentially of an anionic polymer or copolymer, which can be optionally formulated with pharmaceutically customary excipients, which contains an active substance that has a water-solubility as defined in the German Pharmacopeia DAB 10 of at least 30 parts by volume of water for 1 part by weight of the active substance which is embedded in the lipophilic matrix,
  wherein the lipophilic matrix with its active substance is embedded in a matrix made from the mucoadhesive polymer, which matrix comprises a chitosan and is adjusted to pH 5.0-5.5 by means of an acid or a buffer system, and is combined with a film-applied outer coating which begins to dissolve in the range of pH 6.0 to 8.0.

* * * * *

UNITED STATES PATENT AND TRADEMARK OFFICE
CERTIFICATE OF CORRECTION

PATENT NO. : 8,273,375 B2
APPLICATION NO. : 11/572720
DATED : September 25, 2012
INVENTOR(S) : Rosario Lizio et al.

It is certified that error appears in the above-identified patent and that said Letters Patent is hereby corrected as shown below:

Title Page, Item (75)

Inventor: "Rosario Lizio, Rossdof (DE)" should read -- Rosario Lizio, Rossdorf (DE) --

In the Specification

Column 2, Line 58, "it self" should read -- it self, --

Column 4, Lines 4-5, "minutes" should read -- minutes, --

Column 4, Line 20, "0.8" should read -- 0.3 --

Column 4, Line 25, "10-100%" should read -- 10-160% --

Column 4, Line 27, "0.01 - 15wt%" should read -- 0.001 - 15wt% --

Column 4, Lines 62-63, "therehereby" should read -- There, thereby --

Column 5, Line 17, "are no" should read -- are not --

Column 5, Line 48, "capric acids" should read -- capric acid --

Column 5, Line 63, "layer a" should read -- layer a) --

Column 6, Line 1, "55 - 30 wt %" should read -- 55-80 wt % --

Column 6, Line 12, "Hassar" should read -- Hassan --

Column 6, Line 33, "0.5 H" should read -- 0.5 PH --

Signed and Sealed this
Thirtieth Day of July, 2013

Teresa Stanek Rea
*Acting Director of the United States Patent and Trademark Office*

CERTIFICATE OF CORRECTION (continued)
U.S. Pat. No. 8,273,375 B2

Column 7, Line 12, "PH 5.0 - 5.5/" should read -- PH 5.0 - 5.5, --

Column 7, Line 15, "ways" should read -- way, --

Column 7, Line 37, "the duodenum" should read -- (the duodenum) --

Column 7, Line 65, insert -- and -- before "70 wt %"

Column 8, Line 5, "layer a" should read -- layer (a) --

Column 8, Line 37, "outsets" should read -- outset --

Column 9, Line 16, "40 - 60 wt-S" should read -- 40 - 60 wt% --

Column 9, Line 18, "acrylate of he" should read -- acrylate of the --

Column 9, Line 29, "130-55" should read -- 100 - 55 --

Column 9, Line 30, "required" should read -- required, --

Column 10, Line 12, "acids" should read -- acids, --

Column 10, Line 13, "5 - 30 t %" should read -- 5 - 30 wt % --

Column 11, Line 9, after "preparation" insert -- . --

Column 11, Line 10, "unfits" should read -- units --

Column 11, Line 38, "car" should read -- can --

Column 11, Line 49, add -- ) -- after "copolymer"

Column 11, Line 55, "50-120 Sm" should read -- 50-120 μm --

Column 12, Line 1, insert -- , -- before "because"

Column 12, Line 4, insert -- , -- before "which"

Column 12, Line 8, insert -- , -- before "than"

Column 12, Line 52, "DAD 10 at most" should read -- DAB 10 at most --

Column 12, Line 52, add -- , -- after "+ 25%"

Column 12, Line 55, "HLE" should read -- HLB --

Column 12, Line 57, "HLE" should read -- HLB --

Column 12, Line 66, "DAD" should read -- DAB --

Column 13, Lines 26-27, "60 (1979; pp." should read -- 60 (1979), PP. --

Column 13, Line 28, "8$^{th}$ ed; 19833 P." should read -- 8$^{th}$ ed., 1983, P. --

Column 13, Line 33, "HLP" should read -- HLB --

Column 14, Line 25, "$C_1$ -$C_{20}$" should read -- $C_5$ - $C_{20}$ --

Column 14, Line 51, "it car" should read -- it can --

Column 14, Line 57, "023" should read -- 928 --

Column 14, Line 59, "EA - To Dynasan" should read -- E ATO, Dynasan --

Column 15, Line 28, insert -- , -- between "cholesterol" and "glyceryl"

Column 15, Line 29, insert -- , -- after "(Span®80)"

Column 15, Line 30, insert -- , -- after "(Span®40)"

Column 15, Line 33, insert -- , -- after "(Arlacel®83)"

Column 15, Line 39, insert -- , -- after "ethers"

Column 15, Line 43, "Macroaol" should read -- Macrgol --

Column 15, Line 47, "(Tween® 60)/" should read -- (Tween® 60), --

Column 15, Line 54, insert -- , -- after "(Lanette® E)"

Column 15, Lines 59-60, "(sphignomyelin)" should read -- (sphingomyelin) --

Column 16, Line 14, "n0%" should read -- 10% --

Column 16, Line 47, insert -- , -- before "and"

Column 16, Line 54, "e" should read -- e.g. --

Column 17, Line 6, "e.g." should read -- (e.g. --

Column 17, Line 21, "X wt-%" should read -- 1 wt-% --

CERTIFICATE OF CORRECTION (continued)
U.S. Pat. No. 8,273,375 B2

Column 17, Line 29, "(methacrylates" should read -- (meth)acrylates --

Column 17, Line 44, "Georp" should read -- Georg --

Column 17, Line 53, "Coatings" should read -- Coating, --

Column 17, Line 60, insert -- , -- before "but"

Column 18, Line 39, "74" should read -- $\underline{74}$ --

Column 18, Line 47, "S (E110, C.I. 159853, FD&C Yellow 6)" should read -- S(E110, C.I. 15985), FD&C Yellow 6) --

Column 18, Line 48, "Blue 21" should read -- Blue 2 --

Column 18, Line 49, "Yellow 53" should read -- Yellow 5 --

Column 18, Line 51, "E27" should read -- E127 --

Column 18, Line 61, "74" should read -- $\underline{74}$ --

Column 19, Line 33, "car be" should read -- can be --

Column 19, Line 52, "143 (1996)" should read -- $\underline{143}$ (1996) --

Column 20, Line 16, "layer D" should read -- Layer B --

Column 20, Line 28, add -- , -- before "are"

Column 20, Line 61, add -- . -- after "10-20 kN"

Column 21, Line 45, "micron zed" should read -- micronized --

Column 22, Line 9, "poly-mer" should read -- polymer --

Column 22, Line 61, "886 ma" should read -- 866 mg --

Column 23, Line 2, add -- . -- after "acid)"

UNITED STATES PATENT AND TRADEMARK OFFICE
CERTIFICATE OF CORRECTION

PATENT NO. : 8,273,375 B2
APPLICATION NO. : 11/572720
DATED : September 25, 2012
INVENTOR(S) : Rosario Lizio et al.

It is certified that error appears in the above-identified patent and that said Letters Patent is hereby corrected as shown below:

Title Page, Item (75)

Inventor: "Rosario Lizio, Rossdof (DE)" should read -- Rosario Lizio, Rossdorf (DE) --

In the Specification

Column 2, Line 58, "it self" should read -- itself, --

Column 4, Lines 4-5, "minutes" should read -- minutes, --

Column 4, Line 20, "0.8" should read -- 0.3 --

Column 4, Line 25, "10-100%" should read -- 10-160% --

Column 4, Line 27, "0.01 - 15wt%" should read -- 0.001 - 15wt% --

Column 4, Lines 62-63, "therehereby" should read -- There, thereby --

Column 5, Line 17, "are no" should read -- are not --

Column 5, Line 48, "capric acids" should read -- capric acid --

Column 5, Line 63, "layer a" should read -- layer a) --

Column 6, Line 1, "55 - 30 wt %" should read -- 55-80 wt % --

Column 6, Line 12, "Hassar" should read -- Hassan --

This certificate supersedes the Certificate of Correction issued July 30, 2013.

Signed and Sealed this
Twenty-fourth Day of September, 2013

Teresa Stanek Rea
*Deputy Director of the United States Patent and Trademark Office*

CERTIFICATE OF CORRECTION (continued)
U.S. Pat. No. 8,273,375 B2

Column 6, Line 14, "Theological" should read -- rheological --

Column 6, Line 33, "0.5 H" should read -- 0.5 PH --

Column 7, Line 12, "PH 5.0 - 5.5/" should read -- PH 5.0 - 5.5, --

Column 7, Line 15, "ways" should read -- way, --

Column 7, Line 37, "the duodenum" should read -- (the duodenum) --

Column 7, Line 65, insert -- and -- before "70 wt %"

Column 8, Line 5, "layer a" should read -- layer (a) --

Column 8, Line 37, "outsets" should read -- outset --

Column 9, Line 16, "40 - 60 wt-S" should read -- 40 - 60 wt% --

Column 9, Line 18, "acrylate of he" should read -- acrylate of the --

Column 9, Line 29, "130-55" should read -- 100 - 55 --

Column 9, Line 30, "required" should read -- required, --

Column 10, Line 12, "acids" should read -- acids, --

Column 10, Line 13, "5 - 30 t %" should read -- 5 - 30 wt % --

Column 11, Line 9, after "preparation" insert -- . --

Column 11, Line 10, "unfits" should read -- units --

Column 11, Line 38, "car" should read -- can --

Column 11, Line 49, add -- ) -- after "copolymer"

Column 11, Line 55, "50-120 Sm" should read -- 50-120 μm --

Column 12, Line 1, insert -- , -- before "because"

Column 12, Line 4, insert -- , -- before "which"

Column 12, Line 8, insert -- , -- before "than"

Column 12, Line 52, "DAD 10 at most" should read -- DAB 10 at most --

CERTIFICATE OF CORRECTION (continued)
U.S. Pat. No. 8,273,375 B2

Column 12, Line 52, add -- , -- after "+ 25%"

Column 12, Line 55, "HLE" should read -- HLB --

Column 12, Line 57, "HLE" should read -- HLB --

Column 12, Line 66, "DAD" should read -- DAB --

Column 13, Line 2, "suppl. 1993, see Section IV" should read -- Suppl., 1993, see section IV --

Column 13, Line 12, "67/54/EEC Point" should read -- 67/548/EEC Point --

Column 13, Lines 26-27, "60 (1979; pp." should read -- 60 (1979), PP. --

Column 13, Line 28, "8$^{th}$ ed; 19833 P." should read -- 8$^{th}$ ed., 1983, P. --

Column 13, Line 33, "HLP" should read -- HLB --

Column 14, Line 25, "$C_1$ -$C_{20}$" should read -- $C_5$ - $C_{20}$ --

Column 14, Line 51, "it car" should read -- it can --

Column 14, Line 57, "023" should read -- 928 --

Column 14, Line 59, "EA - To Dynasan" should read -- E ATO, Dynasan --

Column 15, Line 28, insert -- , -- between "cholesterol" and "glyceryl"

Column 15, Line 29, insert -- , -- after "(Span®80)"

Column 15, Line 30, insert -- , -- after "(Span®40)"

Column 15, Line 33, insert -- , -- after "(Arlacel®83)"

Column 15, Line 39, insert -- , -- after "ethers"

Column 15, Line 43, "Macroaol" should read -- Macrgol --

Column 15, Line 47, "(Tween® 60)/" should read -- (Tween® 60), --

Column 15, Line 54, insert -- , -- after "(Lanette® E)"

Column 15, Lines 59-60, "(sphignomyelin)" should read -- (sphingomyelin) --

Column 16, Line 14, "n0%" should read -- 10% --

CERTIFICATE OF CORRECTION (continued)

Column 16, Line 23, "pump such" should read -- pump, such --

Column 16, Line 47, insert -- , -- before "and"

Column 16, Line 54, "e" should read -- e.g. --

Column 17, Line 6, "e.g." should read -- (e.g. --

Column 17, Line 21, "X wt-%" should read -- 1 wt-% --

Column 17, Line 29, "(methacrylates" should read -- (meth)acrylates --

Column 17, Line 44, "Georp" should read -- Georg --

Column 17, Line 53, "Coatings" should read -- Coating, --

Column 17, Line 60, insert -- , -- before "but"

Column 18, Line 39, "74" should read -- <u>74</u> --

Column 18, Line 47, "S (E110, C.I. 159853, FD&C Yellow 6)" should read -- S(E110, C.I. 15985), FD&C Yellow 6) --

Column 18, Line 48, "Blue 21" should read -- Blue 2 --

Column 18, Line 49, "Yellow 53" should read -- Yellow 5 --

Column 18, Line 51, "E27" should read -- E127 --

Column 18, Line 61, "74" should read -- <u>74</u> --

Column 19, Line 33, "car be" should read -- can be --

Column 19, Line 52, "143 (1996)" should read -- <u>143</u> (1996) --

Column 20, Line 16, "layer D" should read -- Layer B --

Column 20, Line 26, "lubricants if necessary" should read -- lubricants, if necessary --

Column 20, Line 28, add -- , -- before "are"

Column 20, Line 61, add -- . -- after "10-20 kN"

Column 21, Line 45, "micron zed" should read -- micronized --

Column 22, Line 9, "poly-mer" should read -- polymer --

Column 22, Line 61, "886 ma" should read -- 866 mg --

Column 23, Line 2, add -- . -- after "acid)"